(12) United States Patent
Webster et al.

(10) Patent No.: US 11,691,956 B2
(45) Date of Patent: Jul. 4, 2023

(54) BIO-BASED DIOLS FROM SUSTAINABLE RAW MATERIALS, USES THEREOF TO MAKE DIGLYCIDYL ETHERS, AND THEIR COATINGS

(71) Applicant: NDSU RSEARCH FOUNDATION, Fargo, ND (US)

(72) Inventors: Dean C. Webster, Fargo, ND (US); Mukund P. Sibi, Fargo, ND (US); Catherine A. Sutton, Fargo, ND (US); Deep J. Kalita, Fargo, ND (US); Eric M. Serum, Eau Claire, WI (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 17/623,405

(22) PCT Filed: Jul. 6, 2020

(86) PCT No.: PCT/US2020/040918
§ 371 (c)(1),
(2) Date: Dec. 28, 2021

(87) PCT Pub. No.: WO2021/007171
PCT Pub. Date: Jan. 14, 2021

(65) Prior Publication Data
US 2022/0372009 A1 Nov. 24, 2022

Related U.S. Application Data

(60) Provisional application No. 62/871,387, filed on Jul. 8, 2019.

(51) Int. Cl.
C07D 307/42 (2006.01)
C07D 407/14 (2006.01)
C09D 163/00 (2006.01)
C08G 59/04 (2006.01)
C08G 59/26 (2006.01)

(52) U.S. Cl.
CPC ......... *C07D 307/42* (2013.01); *C07D 407/14* (2013.01); *C08G 59/04* (2013.01); *C08G 59/26* (2013.01); *C09D 163/00* (2013.01)

(58) Field of Classification Search
CPC .. C07D 307/14; C07D 307/42; C07D 303/24; C07D 303/27; C08G 59/04; C08G 59/26; C08G 59/50–60; C08L 63/00; C09D 163/00
See application file for complete search history.

(56) References Cited

U.S. PATENT DOCUMENTS

2003/0055100 A1* 3/2003 Uckun ............... C07D 333/22
514/423
2012/0220742 A1* 8/2012 Cho .................. C08G 59/26
526/270

2013/0295399 A1 11/2013 Schaefer et al.
2016/0152764 A1 6/2016 Jeol
2017/0121317 A1 5/2017 Buffe et al.

FOREIGN PATENT DOCUMENTS

JP 03101671 A * 4/1991
JP 2007238570 A 9/2007
JP 2018193353 A 12/2018

OTHER PUBLICATIONS

Partial machine translation of JP-03101671-A (1991).*
International Search Report and Written Opinion in International Application No. PCT/US2020/040918, dated Sep. 11, 2020.
International Preliminary Report on Patentability in International Application No. PCT/US2020/040918, dated Sep. 11, 2020.
Hu et al., "Mechanically Triggered Small Molecule Release from a Masked Furfuryl Carbonate", Journal of the American Chemical Society, 141: 15018-15023 (2019), and Supporting Information.
PubChem, Substance Record for SID 311663159, Available Date: Feb. 23, 2016 [retrieved on Sep. 9, 2020]. Retrieved from the Internet: <URL: https://pubchem.ncbi.nlm.nih.gov/substance/311663159>.
PubChem, Substance Record for SID 235901493, Available Date: Feb. 13, 2015 [retrieved on Sep. 9, 2020]. Retrieved from the Internet: <URL: https://pubchem.ncbi.nlm.nih.gov/substance/235901493>.
Kucherov et al., ACS Sustainable Chemistry & Engineering 2018, 6(7):8064-8092.
Isikgor et al., Polymer Chemistry 2015, 6(25):4497-4559.
Delidovich et al., Chemical Reviews 2016, 116(3):1540-1599.
Mülhaupt et al., Macromolecular Chemistry and Physics 2013, 214(2):159-174.
Galbis et al., Chemical Reviews 2016, 116(3):1600-1636.
Yu et al., Bioresource Technology 2017, 238:716-732.
Van Putten et al., Chemical Reviews 2013, 113(3):1499-1597.
Jong et al., Biobased Monomers, Polymers, and Materials, American Chemical Society: 2012; vol. 1105, pp. 1-13.
Sousa et al., Polymer Chemistry 2015, 6(33):5961-5983.
Mou et al., ACS Sustainable Chem. Eng. 2016, 4(12):7118-7129.
Li et al., J. Polym. Sci., Part A: Polym. Chem. 2018, 56:968-976.
Li et al., ACS Sustainable Chem. Eng. 2017, 5(12):11752-11760.
Vijamarri et al., ACS Sustainable Chem. Eng. 2018, 6(2):2491-2497.
Rajmohan et al., RSC Advances, 5(121), 100401-100407; 2015.

(Continued)

*Primary Examiner* — Kregg T Brooks
(74) *Attorney, Agent, or Firm* — Raphael Bellum PLLC

(57) ABSTRACT

The invention relates to diols derived from 5-hydroxymethyl furfural, diformyl furan, or derivatives thereof. The invention further relates to diglycidyl ethers derived from the diols of the invention, curable coating compositions containing the diglycidyl ethers, and objects coated with the curable coating compositions. The invention also relates to composites, composites, adhesives, and films containing the diglycidyl ethers of the invention. The invention also relates to methods of making the diols, diglycidyl ethers, and curable coating compositions.

13 Claims, No Drawings

(56) References Cited

OTHER PUBLICATIONS

Fuentes et al., Chemistry Central Journal (2012), 6, 151.
Shen et al., Ind. Eng. Chem. Res. 2017, 56(38):10929-10938.
Ding et al., ACS Sustainable Chem. Eng. 2017, 5(9):7792-7799.
Hu et al., Macromolecules 2014, 47(10):3332-3342.
Finiels et al., "Selective hydroxyethylation of furfuryl alcohol with aqueous acetaldehyde in the presence of H-form zeolites," Abstract 23-P-06 at p. 230 of Zeolites and Mesoporous Materials at the Dawn of the 21st Century: proceedings of the 13th International Zeolite Conference, Montpellier, France Jul. 8-13, 2001; Galameau et al. eds.
Bach et al., in High-Throughput Analysis: A Tool for Combinatorial Materials Science, eds. R. A. Potyrailo and E. J. Amis, Springer US, Boston, MA, 2003, pp. 525-549.
Bach et al., Farbe Lack 2002, 108:30 [discussed in paragraph [0065] of the published application US 2022/0372009].

* cited by examiner

BIO-BASED DIOLS FROM SUSTAINABLE RAW MATERIALS, USES THEREOF TO MAKE DIGLYCIDYL ETHERS, AND THEIR COATINGS

CROSS-REFERENCE TO RELATED APPLICATION

This application claims priority to U.S. Application No. 62/871,387, filed Jul. 8, 2019, which is incorporated herein by reference.

STATEMENT OF U.S. GOVERNMENT SUPPORT

This invention was made with government support under grant IIA-1355466 awarded by the National Science Foundation. The U.S. government has certain rights in the invention.

BACKGROUND

The development of green chemical methods for the synthesis of novel monomers for polymer applications has received intense scrutiny in the past two decades. Furthermore, the use of bio-based feedstocks for monomer synthesis has become important due to the projected depletion of fossil fuels in the near future [Kucherov et al., ACS Sustainable Chemistry & Engineering 2018, 6(7):8064-8092; Isikgor et al., Polymer Chemistry 2015, 6(25):4497-4559; Delidovich et al., Chemical Reviews 2016, 116(3):1540-1599; Mülhaupt et al., Macromolecular Chemistry and Physics 2013, 214(2):159-174; Galbis et al., Chemical Reviews 2016, 116(3):1600-1636]. Diols serve as important monomers for the synthesis of a variety of polymers such as polyesters and polyurethanes. Currently, most of the diols used in polymer applications are derived from petroleum.

Of the three important sources of biomass, cellulosic biomass provides access to compounds with a furan skeleton. Two compounds derived from cellulose, 5-hydroxymethyl furfural (HMF) [Yu et al., Bioresource Technology 2017, 238:716-732; van Putten et al., Chemical Reviews 2013, 113(3):1499-1597] and 2,5-furandicarboxylic acid (FDCA) [Jong et al., Furandicarboxylic Acid (FDCA), A Versatile Building Block for a Very Interesting Class of Polyesters. In Biobased Monomers, Polymers, and Materials, American Chemical Society: 2012; Vol. 1105, pp 1-13; Sousa et al., Polymer Chemistry 2015, 6(33):5961-5983], have been identified as the top feedstock compounds for monomer synthesis. HMF has two functional groups at different oxidation states that can be selectively manipulated to provide access to other furan-based monomers. Diformylfuran (DFF) is readily available by selective oxidation of HMF.

The diols are useful monomers in the synthesis of a variety of polymers [Mou et al., ACS Sustainable Chem. Eng. 2016, 4(12):7118-7129]. For example, they are used extensively in the synthesis of polyesters [Li et al., J. Polym. Sci., Part A: Polym. Chem. 2018, 56:968-976]. Also, the glycidyl ethers derived from diols can be cured with diamines to furnish epoxies. The different diols currently used extensively in polymer synthesis are (1) aliphatic diols, (2) bisphenols, and (3) mixed diols. In contrast, the use of diol monomers derived from cellulosic biomass with a furan skeleton has received only limited attention.

SUMMARY OF THE INVENTION

The invention relates to novel diols derived from 5-hydroxymethyl furfural (HMF), diformyl furan (DFF), or derivatives thereof. The invention also relates to the synthesis of the diols.

The invention further relates to diglycidyl ethers derived from the diols of the invention. The invention also relates to the synthesis of the diglycidyl ethers. The invention also relates to composites and adhesives containing the diglycidyl ethers.

The invention further relates to curable coating compositions containing the diglycidyl ethers with amine curing agents, and object coating with the curable coating compositions.

DETAILED DESCRIPTION OF THE INVENTION

The invention relates to a diol having the following structure:

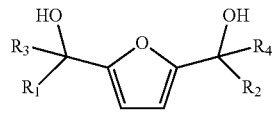

wherein $R_1$, $R_2$, $R_3$, and $R_4$ are independently selected from the group consisting of H, $C_1$-$C_6$alkyl, $C_1$-$C_6$ alkenyl, aryl, and $C_1$-$C_6$alkyl-aryl, with the proviso that the diol cannot have the following structure:

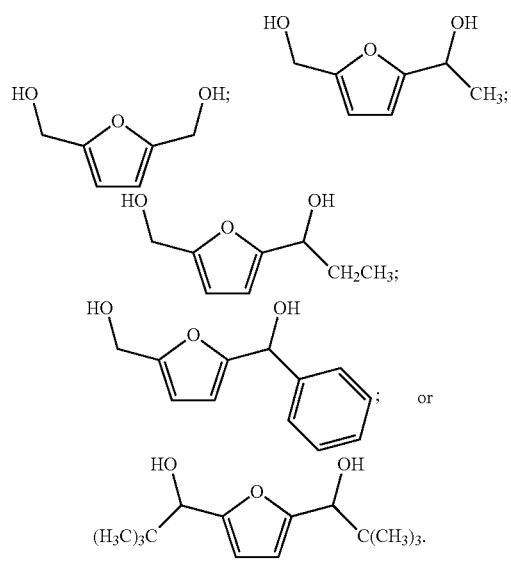

As used herein, the term "alkyl" refers to a linear, branched, saturated hydrocarbon group, such as methyl, ethyl, n-propyl, iso-propyl, n-butyl, iso-butyl, tert-butyl, pentyl, hexyl, and the like.

As used herein, the term "alkenyl" refers to a linear, branched hydrocarbon group containing at least one double bond, such as ethenyl, n-propenyl, iso-propenyl, n-butenyl, iso-butenyl, pentenyl, hexenyl, and the like.

As used herein, the term "aryl" refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 6 to 10 carbon atoms. Exemplary aryl groups contain one aromatic ring or two fused or linked aromatic rings, e.g., phenyl (Ph), naphthyl, biphenyl, diphenylether, diphenylamine, benzophenone, phenanthryl, and the like.

The diol preferably has the following structure:

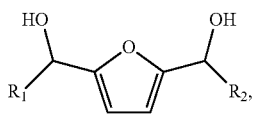

wherein $R_1$ and $R_2$ are as defined above. Preferably, $R_1$ and $R_2$ are both methyl, ethyl, n-butyl, c-pentyl, allyl, or benzyl.

The diol also preferably has the following structure:

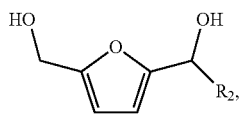

wherein $R_2$ is as defined above. Preferably, $R_2$ is n-butyl, t-butyl, c-pentyl, allyl, or benzyl.

The diol also preferably has the following structure:

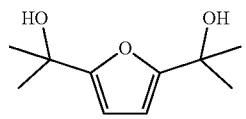

The invention also relates to a method of making the diols of the invention, comprising, consisting essentially of, or consisting of:

reacting 5-hydroxymethyl furfural (HMF), diformyl furan (DFF), or a derivative thereof with a Grignard reagent, under conditions sufficient to form the diol.

Preferably, the Grignard reagent is RMgCl, wherein R is H, $C_1$-$C_6$ alkyl, $C_1$-$C_6$ alkenyl, aryl, or $C_1$-$C_6$ alkyl-aryl.

Preferably, the derivative used in the method of making the diols of the invention has the following structure:

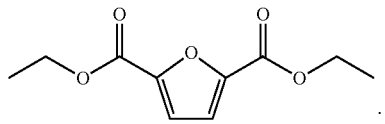

The invention also relates to a diglycidyl ether having the following structure:

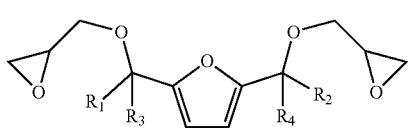

wherein $R_1$, $R_2$, $R_3$, and $R_4$ are independently selected from the group consisting of H, $C_1$-$C_6$ alkyl, $C_1$-$C_6$ alkenyl, aryl, and $C_1$-$C_6$ alkyl-aryl, with the proviso that $R_1$, $R_2$, $R_3$, and $R_4$ cannot all be H.

Preferably, the diglycidyl ethers have the following structure:

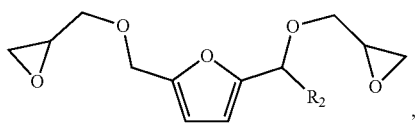

wherein $R_2$ is as defined above. Preferably, $R_2$ is methyl or phenyl.

Preferably, the diglycidyl ethers also have the following structure:

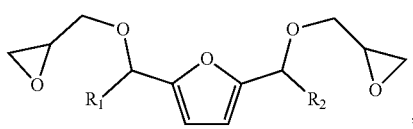

wherein $R_1$ and $R_2$ are as defined above. Preferably, $R_1$ and $R_2$ are both methyl, n-butyl, or allyl.

Preferably, the diglycidyl ether also has following structure:

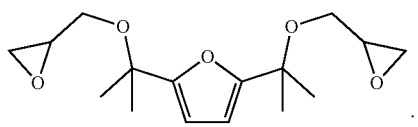 [SMILES: CC(C)(OCC1CO1)c1ccc(C(C)(C)OCC2CO2)o1]

The invention also relates to a method for making the diglycidyl ethers of the invention comprising, consisting essentially of, or consisting of:

reacting a diol with epichlorohydrin under conditions sufficient to form the diglycidyl ether, wherein the diol has the following structure:

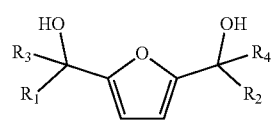

wherein $R_1$, $R_2$, $R_3$, and $R_4$ are independently selected from the group consisting of H, $C_1$-$C_6$ alkyl, $C_1$-$C_6$ alkenyl, aryl, and $C_1$-$C_6$ alkyl-aryl.

Preferably, the diols used in the methods for making the diglycidyl ethers of the invention cannot have the following structure:

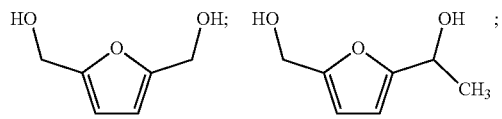

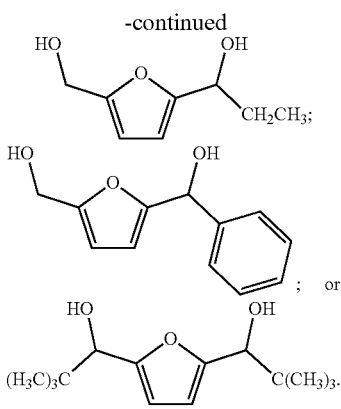

The invention also relates to a coating, composite, adhesive, or film comprising, consisting essentially of, or consisting of at least one diglycidyl ether of the invention.

The invention further relates to a curable coating composition comprising, consisting essentially of, or consisting of:
a) at least one diglycidyl ether of the invention; and
b) an amine.

Preferably, the amine is an aliphatic, an aromatic, a cycloaliphatic, or a polyether amine. For example, the aliphatic amine may be Priamine 1075, 1,8-diaminooctane, diethylenetriamine, or tetraethylenepentamine; the aromatic amine may be m-xylylenediamine; the cycloaliphatic amine may be 1,3-bis(aminomethyl)cyclohexane, isophorone diamine, or bis(p-aminocyclohexyl) methane; and the polyether amine may be JEFFAMINE EDR-148 (XTJ-504), JEFFAMINE D-400, JEFFAMINE D-230, or JEFFAMINE T-403.

The curable coating compositions of the invention may be coated onto a substrate and cured using techniques known in the art. The substrate can be any common substrate such as paper, polyester films such as polyethylene and polypropylene, metals such as aluminum and steel, glass, urethane elastomers, primed (painted) substrates, and the like.

Pigments and other additives known in the art to control coating rheology and surface properties can also be incorporated in a curable coating composition of the invention. For example, a curable coating composition of the invention may further contain coating additives. Such coating additives include, but are not limited to, one or more leveling, rheology, and flow control agents such as silicones, fluorocarbons, or cellulosics; extenders; reactive coalescing aids such as those described in U.S. Pat. No. 5,349,026, incorporated herein by reference; plasticizers; flatting agents; pigment wetting and dispersing agents and surfactants; ultraviolet (UV) absorbers; UV light stabilizers; tinting pigments; colorants; defoaming and antifoaming agents; anti-settling, anti-sag and bodying agents; anti-skinning agents; anti-flooding and anti-floating agents; biocides, fungicides and mildewcides; corrosion inhibitors; thickening agents; or coalescing agents. Specific examples of such additives can be found in Raw Materials Index, published by the National Paint & Coatings Association, 1500 Rhode Island Avenue, N.W., Washington, D.C. 20005. Further examples of such additives may be found in U.S. Pat. No. 5,371,148, incorporated herein by reference.

Solvents may also be added to the curable coating formulation in order to reduce the viscosity. Hydrocarbon, ester, ketone, ether, ether-ester, alcohol, or ether-alcohol type solvents may be used individually or in mixtures. Examples of solvents can include, but are not limited to, benzene, toluene, xylene, aromatic 100, aromatic 150, acetone, methylethyl ketone, methyl amyl ketone, butyl acetate, t-butyl acetate, tetrahydrofuran, diethyl ether, ethylethoxy propionate, isopropanol, butanol, butoxyethanol, etc.

The invention further relates to a cured coating composition, wherein the curable coating composition of the invention is cured at ambient conditions or by heating.

The invention also relates to an object coated with the curable coating composition of the invention.

EXAMPLES

Materials

Commercially available HMF was purified by column chromatography or by dissolving it in diethyl ether and drying with anhydrous sodium sulfate and decolorizing with Norrit A. The compound was stored in a freezer prior to use. Diformylfuran (2) was synthesized by oxidation of pure HMF with manganese dioxide and ethyl acetate as a solvent (Scheme 1). The product was recrystallized from iso-propanol before use.

Scheme 1. Synthesis of diforymylfuran

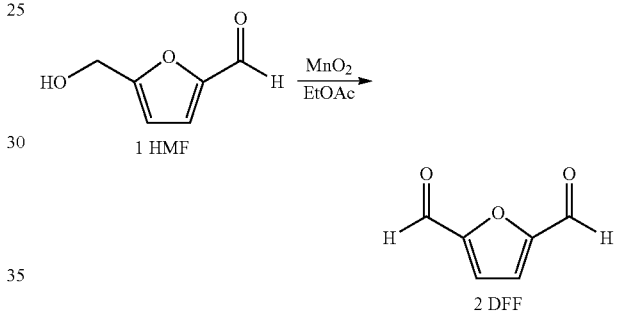

Fischer esterification of 2,5-furandicarboxylic acid (FDCA) 3 with ethanol provided the diethyl ester 4 in high yield. The diol, 2,5-bihydroxymethylfuran (5) was synthesized by sodium borohydride reduction of HMF 1 in ethanol (Scheme 2) [Li et al., ACS Sustainable Chem. Eng. 2017, 5(12):11752-11760; Vijjamarri et al., ACS Sustainable Chem. Eng. 2018, 6(2):2491-2497].

Scheme 2. Synthesis of starting materials

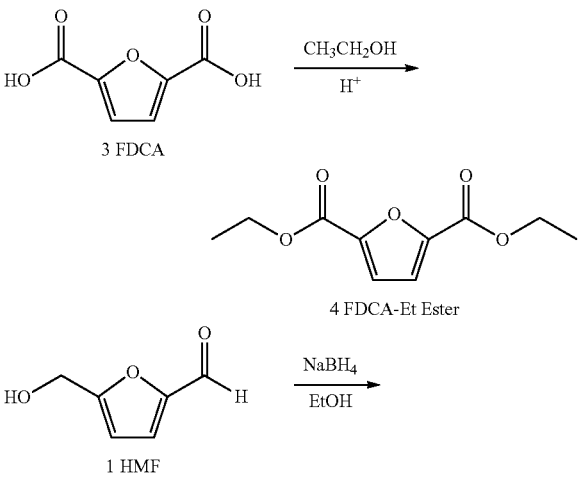

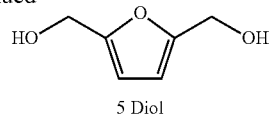

5 Diol

Synthesis of Symmetric and Unsymmetrical Diols

The formyl group in HMF was converted to a secondary alcohol by the addition of a Grignard reagent. Several variables such as solvent, temperature, stoichiometry and counterion of the Grignard reagent were investigated for obtaining the product diols in high purity and yield. Table 1 lists isolated yields for the unsymmetrical diol 6. The table also lists the physical state of the diol. As can be discerned from the table, the diols are obtained in excellent yield from the Grignard addition. Also, most of the compounds have not been reported previously (References are given for known compounds in Table 1). The product diols were extensively characterized by spectroscopic techniques. The synthesis of diols from HMF is shown Scheme 3 ("R" defined in Table 1).

Typical experimental procedure: A reaction vessel containing solution of purchased Grignard reagent (6.6 mmol, diluted from 1.0-3.4 M to a 0.5 M solution in inhibitor-free drysolv THF) was flushed with $N_2$ and kept under positive $N_2$ pressure. A solution of HMF (3 mmol) dissolved to form a 0.2 M solution in inhibitor-free drysolv THF) was added dropwise via syringe into the dry 50 mL round bottom flask reaction vessel. The reaction was monitored by TLC, until the reaction was complete (1-2 h). To quench the reaction, 6 mL of 0.1 M trisodium citrate (aq) was added via syringe. The reaction mixture was filtered through filter paper, then the THF was removed in vacuo. The resulting oil was then diluted with ethyl acetate (40 mL) and washed with brine (10 mL×3) in a 60 mL reparatory funnel. The organic layer was dried over sodium sulfate, then filtered and solvent removed in vacuo to obtain the product.

Scheme 3. Synthesis of unsymmetrical diols from HMF

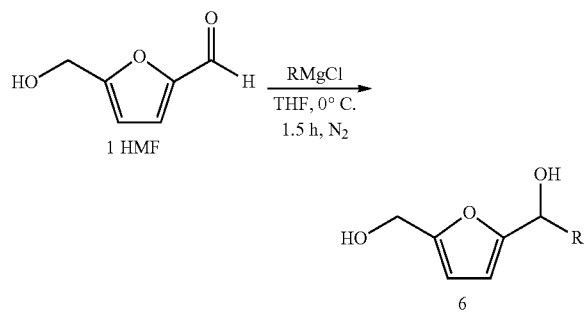

TABLE 1

Synthesis of unsymmetrical Diols from HMF:
Yield and Physical State

| Entry | R | Yield (%) | State | Reference |
|---|---|---|---|---|
| 1 | Methyl (6a) | 77 | liquid | Finiels, A. et al., Studies in Surface Science and Catalysis, 135(Zeolites and Mesoporous Materials at the Dawn of the 21st Century), 3612-3619; 2001 |
| 2 | Ethyl (6b) | 91 | liquid | Nishimura, Shun; Ebitani, Koki, Jpn. Kokai Tokkyo Koho (2018), JP 2018193353 A 20181206. |
| 3 | n-Butyl (6c) | 94 | liquid | — |
| 4 | t-Butyl (6d) | 95 | liquid | — |
| 5 | c-Pentyl (6e) | 78 | liquid | — |
| 6 | Allyl (6f) | 88 | liquid | — |
| 7 | Phenyl (6g) | 87 | solid | Rajmohan, Rajamani et al., RSC Advances, 5(121), 100401-100407; 2015 |
| 8 | Benzyl (6h) | 80 | liquid | — |

HMF Based Diols

Compound 6a: $^1$H (400 MHz, CDCl$_3$) δ 6.20 (d, J=3.2 Hz, 1H), 6.15 (d, J=3.1 Hz, 1H), 4.83 (q, J=6.6 Hz, 1H), 4.54 (s, 2H), 3.01 (s, 2H), 1.51 (d, 6.6 Hz, 3H); $^{13}$C (101 MHz, CDCl$_3$) δ 157.5, 153.3, 108.2, 105.8, 63.3, 57.1, 21.0. FTIR (neat) cm$^{-1}$ 3316, 2979, 2932, 1635, 1557, 1369, 1320, 1239, 1187, 1072. HRMS calculated for C$_7$H$_{10}$O$_3$Na: 165.0528; Found: 165.0537.

Compound 6b: $^1$H (400 MHz, CDCl$_3$) δ 6.17 (d, J=3.2 Hz, 1H), 6.13 (d, J=2.8 Hz, 1H), 4.50 (s, 3H), 3.46 (s, 1H), 3.29 (s, 1H), 1.94-1.75 (m, 2H), 0.93 (t, J=7.4 Hz, 3H); $^{13}$C (101 MHz, CDCl$_3$) δ 156.5, 153.3, 108.7, 106.5, 69.0, 57.0, 28.3, 10.0. FTIR (neat) cm$^{-1}$ 3304, 2965, 2933, 2876, 1556, 1378, 1318, 1242, 1183, 960. HRMS calculated for C$_8$H$_{12}$O$_3$Na: 179.0684; Found: 179.0730.

Compound 6c: $^1$H (400 MHz, CDCl$_3$) δ 6.20 (d, J=3.1 Hz, 1H), 6.15 (d, J=3 Hz, 1H), 4.61 (t, J=6.9 Hz, 1H), 4.53 (s, 2H), 2.93 (s, 1H), 2.82 (s, 1H), 1.83 (dtd, J=8.0, 6.3, 1.2 Hz, 2H), 1.42-1.30 (m, 4H), 0.91 (t, J=7.0 Hz, 3H); $^{13}$C (101 MHz, CDCl$_3$) 5156.9, 153.3, 108.2, 106.4, 67.6, 57.2, 35.0, 27.7, 22.4, 14.0. FTIR (neat) cm$^{-1}$ 3315, 2955, 2931, 2861, 1724, 1559, 1457, 1377, 1243, 1182. HRMS calculated for C$_{10}$H$_{16}$O$_3$Na: 207.0997; Found: 207.0982.

Compound 6d: $^1$H (400 MHz, CDCl$_3$) δ 6.24 (d, J=3.1 Hz, 1H), 6.17 (d, J=3.1 Hz, 1H), 4.57 (s, 2H), 4.35 (s, 1H), 2.25 (s, 2H), 0.98 (s, 9H); $^{13}$C (101 MHz, CDCl$_3$) δ 155.7, 152.8, 108.2, 107.8, 76.4, 57.4, 35.7, 25.8. FTIR (neat) cm$^{-1}$ 3396, 2955, 2870, 1723, 1552, 1479, 1464, 1394, 1364, 1197. HRMS calculated for C$_{10}$H$_{16}$O$_3$Na: 207.0997; Found: 207.0997

Compound 6e: $^1$H (400 MHz, CDCl$_3$) δ 6.19 (d, J=3.1 Hz, 1H), 6.15 (d, J=3.1 Hz, 1H), 4.53 (s, 2H), 4.37 (d, J=8.6 Hz, 1H), 2.85 (s, 1H), 2.74 (s, 1H), 2.37 (q, J=8.1 Hz, 1H), 1.90-1.84 (m, 1H), 1.66-1.47 (m, 6H), 1.25-1.18 (m, 1H); $^{13}$C (101 MHz, CDCl$_3$) δ 156.7, 153.2, 108.2, 106.9, 71.8, 57.3, 44.4, 29.2, 25.5. FTIR (neat) cm$^{-1}$ 3327, 2949, 2867, 1704, 1559, 1449, 1362, 1311, 1885, 931. HRMS calculated for C$_{11}$H$_{16}$O$_3$Na: 219.0997; Found: 219.0999.

Compound 6f: $^1$H (400 MHz, CDCl$_3$) δ 6.19 (d, J=3.2 Hz, 1H), 6.16 (d, J=3.2 Hz, 1H), 5.80 (td, J=17.2, 7.0 Hz, 1H), 5.18-5.11 (m, 2H), 4.67 (t, J=6.5 Hz, 1H), 4.51 (s, 2H), 3.26 (s, 1H), 3.20 (s, 1H), 2.59 (t, J=7.2 Hz, 2H); $^{13}$C (101 MHz, CDCl$_3$) 5156.0, 153.4, 133.8, 118.3, 108.3, 106.8, 66.9, 57.2, 39.8. FTIR (neat) cm$^{-1}$ 3320, 2923, 1641, 1557, 1416, 1316, 1182, 916, 860, 793. HRMS calculated for C$_9$H$_{12}$O$_3$Na: 191.0684; Found: 191.0721.

Compound 6g: $^1$H NMR (400 MHz, DMSO-d6) δ 7.41 (dd, J=8.3, 1.3 Hz, 2H), 7.37-7.32 (m, 2H), 7.30-7.24 (m, 1H), 6.18 (d, J=3.1 Hz, 1H), 6.04 (d, J=3.1 Hz, 1H), 5.96 (d, J=5.0 Hz, 1H), 5.65 (d, J=5.0 Hz, 1H), 5.15 (t, J=5.7 Hz, 1H), 4.33 (d, J=5.7 Hz, 2H); $^{13}$C NMR (101 MHz, DMSO-d6) δ 157.1, 155.1, 143.1, 128.4, 127.6, 127.0, 107.8, 107.3, 68.9, 56.1. FTIR (neat) cm$^{-1}$ 3242, 2881, 1601, 1555, 1491, 1452, 1291, 1263, 1193, 1008. HRMS calculated for $C_{12}H_{12}O_3Na$: 227.0684; Found: 227.0686.

Compound 6h: $^1$H NMR (400 MHz, CDCl$_3$) δ 7.31-7.17 (m, 5H), 6.17 (d, J=3.1 Hz, 1H), 6.12 (d, J=3.1 Hz, 1H), 4.84 (dd, J=7.9, 5.9 Hz, 1H), 4.51 (s, 2H), 3.31 (s, 1H), 3.13 (qd, J=13.7, 6.9 Hz, 2H), 2.76 (s, 1H); $^{13}$C NMR (101 MHz, CDCl$_3$) δ 155.7, 153.4, 137.5, 129.4, 128.4, 126.6, 108.4, 107.1, 68.6, 57.2, 42.0. FTIR (neat) cm$^{-1}$ 3379, 3027, 2922, 1702, 1602, 1495, 1453, 1416, 1360, 1221. HRMS calculated for $C_{13}H_{14}O_3Na$: 241.0841; Found: 241.0839.

Reaction of DFF 2 with excess Grignard reagent gave access to diols 7 (Scheme 4) ("R" defined in Table 2). Table 2 lists the isolated yield of the symmetric diols. As can be seen from the table, the diols are produced in high yields and all of them are liquids. Another noteworthy feature of the diols is that most of them are new compounds. The diols are produced as a mixture of meso and DL products. The products were extensively characterized by spectroscopic techniques. No attempt was made to ascribe chemical shifts to meso and DL products.

Typical experimental procedure: A reaction vessel containing solution of purchased Grignard reagent (6.6 mmol, diluted from 1.0-3.4 M to a 0.5 M solution in inhibitor-free drysolv THF) was flushed with N$_2$ and kept under positive N$_2$ pressure. A solution of DFF (3 mmol) dissolved to form a 0.2 M solution in inhibitor-free drysolv THF) was added dropwise via syringe into the dry 50 mL round bottom flask reaction vessel. The reaction was monitored by TLC, until the reaction was complete (1-2 h). To quench the reaction, 6 mL of 0.1 M trisodium citrate (aq) was added via syringe. The reaction mixture was filtered through filter paper, then the THF was removed in vacuo. The resulting oil was then diluted with ethyl acetate (40 mL) and washed with brine (10 mL×3) in a 60 mL reparatory funnel. The organic layer was dried over sodium sulfate, then filtered and solvent removed in vacuo to obtain the product.

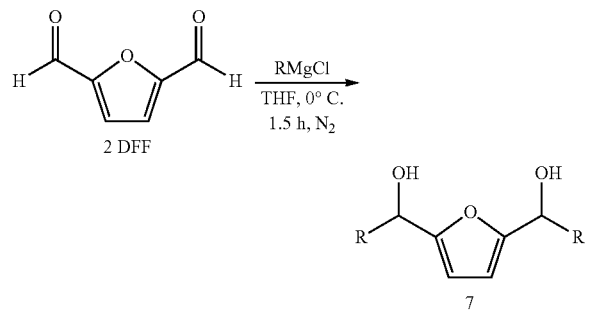

Scheme 4. Synthesis of symmetrical diols from DDF

TABLE 2

Synthesis of symmetrical diols from DFF: Yield and Physical State

| Entry | R | Yield (%) | State | Reference |
|---|---|---|---|---|
| 1 | Methyl (7a) | 98 | liquid | — |
| 2 | Ethyl (7b) | 95 | liquid | — |
| 3 | n-Butyl (7c) | 90 | liquid | — |
| 4 | t-Butyl (7d) | 94 | liquid | Fuentes, Jose A. et al., Chemistry Central Journal (2012), 6,151. |
| 5 | c-Pentyl (7e) | 95 | liquid | — |
| 6 | Allyl (7f) | 80 | liquid | — |
| 7 | Benzyl (7g) | 83 | liquid | — |

DFF-Based Diols

Compound 7a: $^1$H (400 MHz, CDCl$_3$) δ 6.15 (d, J=1.3 Hz, 2H), 4.84 (q, J=6.6 Hz, 2H), 2.79 (s, 2H), 1.52 (d, J=6.6 Hz, 6H); $^{13}$C (101 MHz, CDCl$_3$) δ 156.9, 105.6, 63.5, 21.0. FTIR (neat) cm$^{-1}$ 3391, 2980, 2934, 1764, 1702, 1446, 1370, 1302, 1238, 1192. HRMS calculated for $C_8H_{12}O_3Na$: 179.0684; Found: 179.0713.

Compound 7b: $^1$H (400 MHz, CDCl$_3$) δ 6.13 (s, 2H), 4.51 (t, J=6.8 Hz, 2H), 2.94 (s, 2H), 1.86-1.79 (h, 7.2 Hz, 4H), 0.93 (t, J=7.4 Hz, 6H); $^{13}$C (101 MHz, CDCl$_3$) δ 195.9, 106.3, 69.0, 28.4, 9.9. FTIR (neat) cm$^{-1}$ 3316, 2964, 2934, 2876, 1557, 1456, 1377, 1315, 1187, 1094. HRMS calculated for $C_{10}H_{16}O_3Na$: 207.0997; Found: 207.1007.

Compound 7c: $^1$H (400 MHz, CDCl$_3$) δ 6.19 (d, J=3.1 Hz, 1H), 6.14 (d, J=3.1 Hz, 1H), 4.60 (t, J=6.9 Hz, 2H), 2.96 (s, 2H), 1.83 (q, J=7.4 Hz, 4H), 1.44-1.29 (m, 8H), 0.91 (t, J=7.0 Hz, 6H); $^{13}$C (101 MHz, CDCl$_3$) δ 156.0, 106.1, 67.4, 36.9, 27.7, 22.4, 13.9. FTIR (neat) cm$^{-1}$ 3337, 2955, 2930, 2860, 1725, 1557, 1457, 1376, 1242, 1104. HRMS calculated for $C_{14}H_{24}O_3Na$: 263.1623; Found: 263.1639.

Compound 7d: $^1$H NMR (400 MHz, CDCl$_3$) δ 6.19 (s, 1H), 6.17 (s, 1H), 4.36 (s, 1H), 4.34 (s, 1H), 2.49 (s, 2H), 0.97 (m, 18H); $^{13}$C NMR (101 MHz, CDCl$_3$) δ 154.6, 107.5, 76.4, 35.7, 25.8. FTIR (neat) cm$^{-1}$ 3429, 3101, 2956, 2871, 1561, 1513, 1413, 1365, 1241, 1189. HRMS calculated for $C_{14}H_{24}O_3Na$: 263.1623; Found: 263.1628.

Compound 7e: $^1$H (400 MHz, CDCl$_3$) δ 6.20 (d, J=3.1 Hz, 1H), 6.15 (d, J=3.1 Hz, 1H), 4.53 (s, 1H), 4.37 (d, J=8.7 Hz, 1H), 2.86 (s, 1H), 2.72 (s, 1H), 2.37 (q, J=8.2 Hz, 2H), 1.91-1.85 (m, 2H), 1.65-1.47 (m, 12H), 1.25-1.19 (m, 2H); $^{13}$C (101 MHz, CDCl$_3$) δ 156.6, 153.2, 108.2, 106.9, 71.8, 57.3, 44.4, 29.3, 29.2, 25.6, 25.5. FTIR (neat) cm$^{-1}$ 3332, 2951, 2867, 1710, 1650, 1450, 1187, 1011, 794, 622. HRMS calculated for $C_{16}H_{24}O_3Na$: 287.1623; Found: 287.1623.

Compound 7f: $^1$H (400 MHz, CDCl$_3$) δ 6.20 (s, 2H), 5.88-5.76 (m, 2H), 5.21 (q, 1.8 Hz, 2H), 5.17 (m, 1H), 5.14 (m, 1 Hf), 4.73 (t, J=5.9 Hz, 3H), 2.62 (m, 3H), 2.39 (s, 2H); $^{13}$C (101 MHz, CDCl$_3$) δ 155.4, 133.8, 118.3, 106.6, 66.9, 39.9. FTIR (neat) cm$^{-1}$ 3309, 3076, 2914, 1640, 1431, 1310, 1186, 859, 794, 643. HRMS calculated for $C_{12}H_{16}O_3Na$: 231.0997; Found: 231.1004.

Compound 7g: $^1$H NMR (400 MHz, CDCl$_3$) δ 7.39-7.20 (m, 10H), 6.15 (d, J=3.1 Hz, 2H), 4.91 (ddd, J=8.0, 5.6, 3.8 Hz, 2H), 3.20-3.10 (s, 4H), 1.91 (s, 2H); $^{13}$C NMR (101 MHz, CDCl$_3$) δ 155.2, 137.3, 129.4, 128.5, 126.7, 107.1, 68.7, 42.1. FTIR (neat) cm$^{-1}$ 3346, 2955, 2905, 2869, 1682, 1557, 1479, 1462, 1389, 1365. HRMS calculated for $C_{20}H_{20}O_3Na$: 331.1310; Found: 331.1311.

Synthesis of Glycidyl Ethers

The formation of glycidyl ethers began by synthesizing a known compound as shown in Scheme 5. Treatment of bishydroxymethylfuran 5 with epichlorohydrin, 50% NaOH, tetra n-butylammonium bromide (TBABr, catalyst) at 50° C. gave the diglycidyl ether 8 in 85% isolated yield. The physical and spectral characteristics of 8 were in complete agreement with those reported in the literature [Shen et al., *Ind. Eng. Chem. Res.* 2017, 56(38):10929-10938; Ding et al., *ACS Sustainable Chem. Eng.* 2017, 5(9):7792-7799; Hu et al., Macromolecules 2014, 47(10):3332-3342].

Typical experimental procedure:

Scheme 5. Synthesis of diglycidyl ether from 2,5-bishydroxymethylfuran

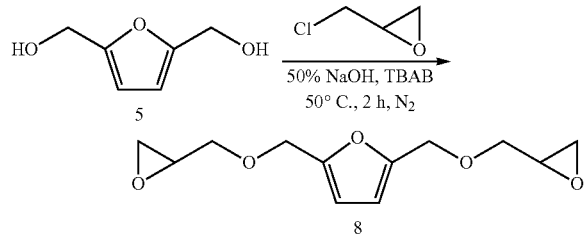

Compound 8: $^1$H NMR (400 MHz, CDCl$_3$) δ 6.31 (s, 2H), 4.58-4.43 (m, 4H), 3.78 (dd, J=11.5, 3.1 Hz, 2H), 3.46 (dd, J=11.5, 5.9 Hz, 2H), 3.17 (ddt, J=5.8, 4.1, 2.9 Hz, 2H), 2.81 (dd, J=5.0, 4.2 Hz, 2H), 2.63 (dd, J=5.0, 2.7 Hz, 2H); $^{13}$C NMR (101 MHz, CDCl$_3$) δ 151.8, 110.3, 70.7, 65.1, 50.7, 44.3; FTIR (neat) cm$^{-1}$ 2930, 2871, 1734, 1636, 1457, 1373, 1243, 1090, 929, 855.

After establishing reaction conditions for glycidation, the synthesis of diglycidyl ethers of unsymmetrical diols 6 was undertaken (Scheme 6) ("R" defined in Table 3). The goal was to prepare a diverse set of diglycidyl ethers and evaluate them in epoxy formation using different diamines. The reaction with diol 6 was optimized to obtain the diglycidyl ether 9 in high yield (Table 3). The products were characterized by spectroscopy. The NMR spectra of the products were complex because of the presence of multiple chiral centers. Two different sources for epichlorohydrin were evaluated. A 100% biobased epichlorohydrin gave diglycidyl ethers with a better impurity profile.

Typical experimental procedure: A 50 mL round bottom flask reaction vessel under N$_2$, containing 50 w/v % NaOH, aq. (4.0 g in 4 mL DI H$_2$O), tetrabutylammonium bromide (32.2 mg, 0.1 mmol) and epichlorohydrin (20 mL) was placed in a 50° C. water bath. Before stirring and placing reaction vessel into hot oil bath, a solution of diol (1 mmol) in epichlorohydrin (10 mL) was added to the reaction vessel dropwise. The vessel was lowered into the hot oil bath (50° C.) and stirring started. The reaction was monitored via TLC, and upon completion (2-14 h), the hot reaction mixture was poured over ice. The resulting liquid was transferred to a 125 mL reparatory funnel and diluted with ethyl acetate (40 mL). Then the aqueous layer was removed and the organic layer was washed with brine (20 mL×3). The organic layer was dried over magnesium sulfate, filtered through filter paper, and then the organic solvent was removed in vacuo to obtain the diglycidyl ether.

Scheme 6. Synthesis of diglycidyl ethers from diols 6

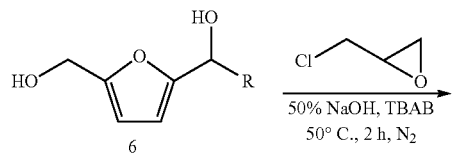

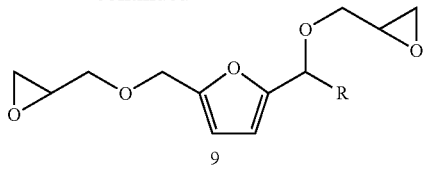

TABLE 3

Diglycidyl ethers derived from unsymmetrical diols 6

| ENTRY | R | YIELD (%) |
|---|---|---|
| 1 | Methyl (9a) | 92 |
| 2 | Phenyl (9b) | 80 |

HMF-Based Diglycidyl Ethers

Compound 9a: $^1$H NMR (400 MHz, CDCl$_3$) δ 6.28 (d, J=3.0 Hz, 1H), 6.23 (d, J=3.2 Hz, 1H), 4.56-4.43 (m, 3H), 3.76 (dd, J=12.3, 3.1 Hz, 1H), 3.65 (ddd, J=20.7, 11.4, 3.3 Hz, 1H), 3.48-3.29 (m, 2H), 3.15 (dq, J=6.0, 3.0 Hz, 1H), 3.10 (dq, J=7.6, 3.9, 3.3 Hz, 1H), 2.80-2.75 (m, 2H), 2.63-2.52 (m, 2H), 1.52 (dd, J=8.6, 6.6 Hz, 3H); BC NMR (101 MHz, CDCl$_3$) δ 155.7, 155.5, 151.1, 151.0, 110.1, 110.0, 107.9, 107.7, 71.1, 71.0, 70.6, 69.5, 68.6, 65.1, 50.9, 50.7, 44.6, 44.4, 44.2, 19.7, 19.5; $^{13}$C-DEPT-135 (101 MHz, CDCl$_3$) δ 110.0 (CH$_2$), 107.9 (CH$_2$), 107.7 (CH$_2$), 71.1 (CH$_2$), 71.0 (CH/CH$_3$), 69.5 (CH/CH$_3$), 68.6 (CH/CH$_3$), 65.1 (CH/CH$_3$), 50.7 (CH$_2$), 44.6 (CH/CH$_3$), 44.4 (CH/CH$_3$), 44.2 (CH/CH$_3$), 19.7 (CH$_2$), 19.7 (CH$_2$); $^1$H—$^{13}$C HSQC (400 MHz/101 MHz, CDCl$_{13}$) δ (6.28, 110.1), (6.23, 107.8), (4.54, 71.1), (4.50, 65.1), (3.77, 70.6), (3.68, 69.5), (3.44, 70.6), (3.33, 69.5), (3.15, 50.7), (2.78, 44.3), (2.62, 44.3), (2.54, 44.4), (1.52, 19.7). FTIR (neat) cm$^{-1}$ 2986, 2867, 1711, 1443, 1372, 1322, 1252, 1090, 1013, 911. HRMS calculated for C$_{13}$H$_{18}$O$_5$Na: 277.1052; Found: 277.1062.

Compound 9b: $^1$H NMR (400 MHz, CDCl$_3$) δ 7.45-7.29 (m, 5H), 6.26 (d, J=3.1 Hz, 1H), 6.11-6.06 (m, 1H), 5.48 (d, J=2.8 Hz, 1H), 4.54-4.44 (m, 2H), 3.75 (ddd, J=18.9, 11.4, 3.2 Hz, 2H), 3.58-3.38 (m, 2H), 3.22-3.11 (m, 2H), 2.80-2.75 (m, 2H), 2.62-2.56 (m, 2H); $^{13}$C NMR (101 MHz, CDCl$_3$) δ 154.6, 154.5, 151.6, 138.7, 138.6, 128.4, 128.1, 128.1, 127.3, 127.1, 110.2, 109.5, 109.3, 77.5, 70.5, 69.8, 69.5, 65.1, 50.8, 50.6, 44.4; $^{13}$C-DEPT-135 (101 MHz, CDCl$_3$) δ 128.4 (CH/CH$_3$), 127.3 (CH/CH$_3$), 127.1 (CH/CH$_3$), 110.2 (CH/CH$_3$), 109.5 (CH/CH$_3$), 109.3 (CH/CH$_3$), 77.5 (CH/CH$_3$), 70.5 (CH$_2$), 69.8 (CH$_2$), 69.56 (CH$_2$), 65.1 (CH$_2$), 50.7 (CH/CH$_3$), 50.6 (CH/CH$_3$), 44.4 (CH$_2$); $^1$H—$^{13}$C HSQC (400 MHz/101 MHz, CDCl$_3$) δ (7.44, 127.2), (7.37, 128.2), (6.27, 110.2), (6.09, 109.5), (5.48, 77.5), (4.49, 65.1), (3.76, 69.6), (3.74, 70.5), (3.62, 69.8), (3.55, 70.5), (3.48, 69.6), (3.42, 70.5), (3.20, 50.7), (3.13, 50.6), (2.77, 44.4), (2.59, 44.3). FTIR (neat) cm$^{-1}$ 2998, 2921, 1555, 1494, 1452, 1334, 1252, 1060, 1021, 845. HRMS calculated for C$_{18}$H$_{20}$O$_5$Na: 339.1208; Found: 339.1208.

The diglycidyl ethers of symmetrical diols 7 were also synthesized (Scheme 7) ("R" defined in Table 4). The reactions were slightly less efficient as compared to reactions with unsymmetrical diols (Table 4). The products were fully characterized by spectroscopy.

Scheme 7. Synthesis of diglycidyl ethers from diols 7

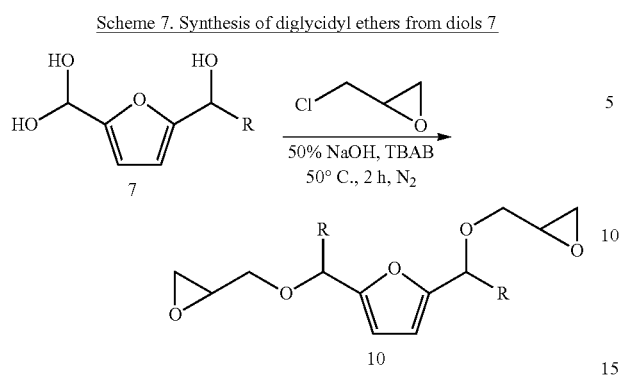

TABLE 4

Diglycidyl ethers derived from symmetrical diols 7

| ENTRY | R | YIELD (%) |
|---|---|---|
| 1 | Methyl (10a) | 65 |
| 2 | Allyl (10b) | 74 |
| 3 | n-Butyl (10c) | 82 |

DFF-Based Diglycidyl Ethers

Compound 10a: $^1$H NMR (400 MHz, CDCl$_3$) δ 6.22 (s, 2H), 4.54 (p, J=6.5 Hz, 2H), 3.64 (ddd, J=16.4, 11.4, 3.3 Hz, 2H), 3.54-3.30 (m, 2H), 3.15-3.06 (m, 1H), 2.84-2.74 (m, 2H), 2.63 (dd, J=4.8, 2.8 Hz, 2H), 2.59-2.51 (m, 1H), 1.59-1.46 (t, 1=6.6 Hz, 6H); $^{13}$C-DEPT-135 (101 MHz, CDCl$_3$) δ 155.0, 107.6, 71.1, 69.5, 68.6, 50.9, 44.4, 19.4; FTIR (neat) cm$^{-1}$ 3061, 2985, 2928, 2864, 1446, 1372, 1253, 1089, 913, 851. HRMS calculated for C$_{14}$H$_{20}$O$_5$Na: 291.1208; found:

Compound 10b: $^1$H NMR (400 MHz, CDCl$_3$) δ 6.25 (q, J=1.6 Hz, 2H), 5.76 (dqd, J=17.2, 6.9, 3.5 Hz, 2H), 5.18-4.96 (m, 4H), 4.48-4.34 (m, 2H), 3.72-3.55 (m, 2H), 3.47 (dt, J=11.5, 4.4 Hz, 1H), 3.32 (ddd, J=11.4, 6.1, 2.4 Hz, 1H), 3.11 (tt, J=8.5, 4.8 Hz, 1H), 2.78 (q, J=4.7 Hz, 2H), 2.75-2.49 (m, 6H); $^{13}$C NMR (101 MHz, CDCl$_3$) δ 153.7, 133.8, 117.4, 108.8, 108.6, 75.1, 75.0, 69.6, 68.8, 50.8, 50.6, 44.6, 44.3, 38.5; $^{13}$C-DEPT-135 (101 MHz, CDCl$_3$) δ 133.9 (CH$_2$), 117.4 (CH/CH$_3$), 108.9 (CH$_2$), 108.6 (CH$_2$), 75.2 (CH$_2$), 74.9 (CH$_2$), 69.6 (CH/CH$_3$), 68.7 (CH/CH$_3$), 50.9 (CH$_2$), 50.6 (CH$_2$), 44.6 (CH/CH$_3$), 44.3 (CH/CH$_3$), 38.5 (CH/CH$_3$); $^1$H—$^{13}$C HSQC (400 MHz/101 MHz, CDCl$_{13}$) δ (6.25, 108.8), (5.76, 133.7), (5.12, 117.3), (5.06, 117.3), (4.40, 75.0), (3.71, 69.5), (3.59, 68.8), (3.48, 68.7), (3.33, 69.5), (3.10, 50.8), (2.79, 44.5), (2.68, 38.5), (2.64, 44.5), (2.53, 44.3). FTIR (neat) cm$^{-1}$ 3074, 2998, 2918, 1641, 1431, 1316, 1252, 1160, 1190, 992. HRMS calculated for C$_{18}$H$_{24}$O$_5$Na: 343.1521; found: 343.1519.

Compound 10c: $^1$H NMR (400 MHz, CDCl$_3$) δ 6.21 (t, J=1.8 Hz, 2H), 4.31 (dt, J=13.8, 7.0 Hz, 2H), 3.65-3.50 (m, 2H), 3.48-3.35 (m, 2H), 3.29 (ddt, J=11.4, 6.1, 1.8 Hz, 2H), 3.08 (tq, J=7.9, 3.8 Hz, 2H), 2.75 (q, J=4.9 Hz, 2H), 2.60 (dd, J=5.1, 2.7 Hz, 2H), 2.50 (dt, J=5.1, 2.7 Hz, 4H), 1.97-1.72 (m, 4H), 1.44-1.10 (m, 6H), 0.87 (t, J=7.1 Hz, 2H); $^{13}$C NMR (101 MHz, CDCl$_3$) δ 154.2, 108.3, 75.4, 69.5, 68.7, 50.9, 50.6, 44.6, 44.3, 33.7, 27.7, 22.4, 13.9; $^{13}$C-DEPT-135 (101 MHz, CDCl$_3$) δ 108.5 (CH/CH$_3$), 75.7 (CH/CH$_3$), 69.5 (CH$_2$), 68.7 (CH$_2$), 50.9 (CH/CH$_3$), 50.6 (CH/CH$_3$), 44.6 (CH$_2$), 44.3 (CH$_2$), 33.7 (CH$_2$), 27.7 (CH$_2$), 22.44 (CH$_2$), 13.9 (CH/CH$_3$); $^1$H—$^{13}$C HSQC (400 MHz/ 101 MHz, CDCl$_{13}$) δ (6.21, 108.0), (4.32, 75.5), (3.62, 69.5), (3.54, 68.7), (3.45, 68.7), (3.29, 69.5), (3.07, 50.8), (2.75, 44.5), (2.60, 44.6), (2.50, 44.3), (1.89, 33.7), (1.82, 33.7), (1.34, 27.7), (1.33, 22.4), (1.21, 27.6), (0.88, 14.0). FTIR (neat) cm$^{-1}$ 2955, 2930, 2861, 1466, 1379, 1320, 1253, 1090, 1013, 795. HRMS calculated for C$_{20}$H$_{32}$O$_5$Na: 375.2147; found: 375.2146.

A tertiary diol 11 was synthesized from by the addition of excess methylmagnesium chloride to FDCA diethyl ester 4 in 85% yield (Scheme 7). The solid diol was not stable and underwent dehydration readily. However, the compound could be stored in a freezer without decomposition.

Scheme 7. Synthesis of a tertiary diol

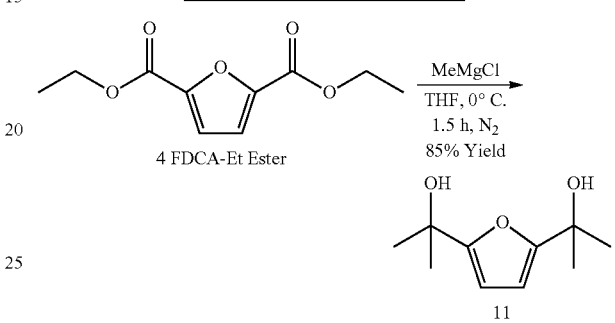

Procedure: A reaction vessel containing solution of purchased Grignard reagent (13.5 mmol eq, diluted from 1.0-3.4 M to a 0.5 M solution in inhibitor-free drysolv THF) was flushed with N$_2$ and kept under positive N$_2$ pressure. A solution of substrate (3 mmol, dissolved to form a 0.1 M solution in inhibitor-free drysolv THF) was added dropwise via syringe into the dry 50 mL round bottom flask reaction vessel. The reaction was monitored by TLC, until the reaction was complete (1-2 h). To quench the reaction, 6 mL of 0.1 M trisodium citrate (aq) was added via syringe. The reaction mixture was filtered through filter paper, then the THF was removed in vacuo. The resulting oil was then diluted with ethyl acetate (40 mL) and washed with brine (10 mL×3) in a 60 mL reparatory funnel. The organic layer was dried over sodium sulfate, then filtered, and solvent removed in vacuo to obtain the diol product in 85% yield.

Compound 11: $^1$H (400 MHz, CDCl$_3$) δ 6.09 (s, 2H), 2.49 (s, 2H), 1.58 (s, 12H); $^{13}$C (101 MHz, CDCl$_3$) δ 159.0, 104.0, 68.7, 28.5. FTIR (neat) cm$^{-1}$ 3362, 2979, 2900, 1375, 1267, 1164, 1115, 1022, 959, 840. HRMS calculated for C$_{10}$H$_{16}$O$_3$Na: 207.0997; Found: 207.0994.

The glycidation of 11 to provide diglycidyl ether 12 was successful and gave the product in 75% yield (Scheme 8). It is interesting to note highly hindered ether such as 12 could be accessed. However, the glycidation was slow as compared to reactions with less hindered alcohols.

Scheme 8. Synthesis of a diglycidyl ether from a tertiary diol

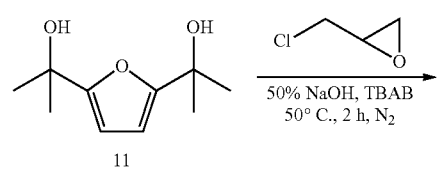

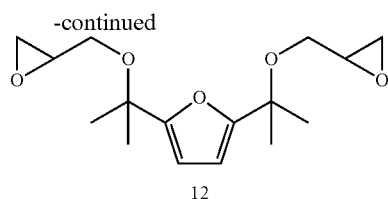

12

Compound 12: $^1$H NMR (400 MHz, CDCl$_3$) δ 6.17 (d, J=3.2 Hz, 1H), 6.12 (d, J=3.2 Hz, 1H), 3.37 (dd, J=11.0, 3.7 Hz, 2H), 3.22 (dd, J=11.0, 5.5 Hz, 2H), 3.06-2.99 (m, 2H), 2.75 (t, 5 Hz, 2H), 2.53 (dd, J=5.1, 2.7 Hz, 2H), 1.59 (s, 6H), 1.56 (s, 6H); $^{13}$C NMR (101 MHz, CDCl$_3$) δ 159.87, 155.8, 107.5, 103.7, 73.3, 68.7, 64.4, 51.0, 44.9, 28.5, 25.7. FTIR (neat) cm$^{-1}$ 2968, 2905, 1375, 1350, 1252, 1168, 1112, 1018, 963, 837. HRMS calculated for C$_{16}$H$_{24}$O$_5$Na: 319.1521; found: 319.1513.

Reaction of Diglycidyl Ethers with Diamines

To evaluate the curing ability of the diglycidyl ether bis-epoxymonomers with four different types of amine curatives, high throughput and conventional methods were used to extract maximum property information of the crosslinked networks with minimal material in a short period of time. The properties of the networks formed from the novel diglycidyl ether bis-epoxymonomers as a function of curative type, cure temperature, and time of curing are disclosed. For comparison, commercial BPA based epoxy resin EPON 828 (Momentive) was used as reference. To evaluate the relative crosslink density of the crosslink networks high throughput dye extraction and nano-indentation technique were used. Conventional methods such as König pendulum hardness and differential scanning calorimetry (DSC) were used to further evaluate the crosslinked networks.

1.1. Materials

The materials used are described in Table 5.

TABLE 5

| Starting materials | | |
|---|---|---|
| Chemical | Designation | Vendor |
| Bisphenol A diglycidyl ether | EPON 828 | Momentive |
| Perylene, 98+% | Perylene | Alfa Aesar |
| Toluene | Toluene | BDH Chemicals |
| Methyl ethyl ketone, 99% | MEK | Alfa Aesar |
| Perylene, 98+%, | Perylene | Alfa Aesar |
| Aluminum panels 4" × 8" | Aluminum panels | Q-LAB |
| polypropylene microtiter plates | | Evergreen Scientific. |

1.2. Preparation of Formulations

Formulations from the diglycidyl ether bis-epoxymonomers and EPON 828 were prepared with four types of amine curatives (total twelve amine curatives listed in Table 6) to investigate the reactivity of the diglycidyl ether bis-epoxymonomers towards different amine curatives and simultaneously the impact of the nature of amine curative on the properties of the cured coatings. To evaluate the relative performance of curatives towards crosslinking, the dye extraction method previously reported by Bach et al. [Bach et al., *Farbe Lack* 2002, 108:30; 2. Bach et al., in *High-Throughput Analysis: A Tool for Combinatorial Materials Science*, eds. R. A. Potyrailo and E. J. Amis, Springer US, Boston, Mass., 2003, pp. 525-549.] was used. Prior to making formulations, a 3 mM solution of perylene dye in toluene was prepared. A representative procedure for making dye incorporated formulation of EPON 828 with isophorone diamine as curative is as follows: 1.14 g of EPON 828 resin was transferred into a 20 mL glass vial, where, 2.56 mL of methyl ethyl ketone (MEK) solvent and 202 μL of perylene dye solution were subsequently added and mixed using Teflon coated magnetic stir bar at 900 rpm on multi-position magnetic stirring plates for 25 min. Next, 0.26 g of isophorone diamine (Epoxy to amine ratio was 1:1) was added to the mixture and mixed for another 20 min prior to deposition on primed aluminum discs. For all the formulations and the amount of dye per formulation unit volume was kept constant.

TABLE 6

List of amine curatives used to study properties of crosslinked networks.

| Type | Name of curative | Designation | Amine hydrogen equivalent weight (AHEW) | Vendors |
|---|---|---|---|---|
| Aliphatic | Priamine 1075 | Priamine | 267 | Croda |
| | 1,8-Diaminooctane | 1,8-DA Octane | 36.07 | Sigma Aldrich |
| | Diethylenetriamine | DETAA | 20.63 | Sigma Aldrich |
| | Tetraethylenepentamine | TEPAA | 24.37 | Sigma Aldrich |
| Aromatic | m-Xylylenediamine | Xylene DA | 34.05 | Sigma Aldrich |
| Cyclo-aliphatic | 1,3-Bis(Aminomethyl)cyclohexane | 1,3 BAC | 35.55 | Mitsubishi gas chemicals |
| | Isophorone diamine | IPDA | 42.68 | |
| | bis(p-aminocyclohexyl)methane | PACM | 52.5 | Sigma Aldrich |
| Polyether | JEFFAMINE EDR-148 (XTJ-504) | XTJ-504 | 37.05 | Huntsman Corporation |
| | JEFFAMINE D-400 | Jeff. D-400 | 115 | Huntsman Corporation |
| | JEFFAMINE D-230 | Jeff. D-230 | 60 | Huntsman Corporation |
| | JEFFAMINE T-403 | Jeff, t-403 | 81 | Huntsman Corporation |

2. Methods and Instruments

2.1. Dye Extraction

Preparation for the dye extraction method was carried out by punching out 10 mm epoxy primed aluminum discs and affixing them to a 4"×8" aluminum panel in a 6×11 array format. 75 μL of each formulation was deposited on six discs using an Eppendorf repeat pipettor. Coatings were then allowed to dry overnight under ambient conditions. Array panels were then cured at room temperature for 7 days, 60° C. and 100° C. using preheated oven for 1 h., 3 h., or 6 h. to evaluate the optimum curing condition. After curing, three discs from each set (same formulation and curing regime) were transferred into 24 well (6×4) polypropylene microtiter plates, each row of wells containing two sets of discs. The discs were affixed to the bottom of each well with double-sided tape and were allowed to adhere for 18+ hours prior to dye extraction.

Dye extraction was performed by adding 500 μL of toluene to each well of the microtiter plate using an Eppendorf repeat pipettor. Toluene was quickly added to each row of the microtiter plate with 15 s intervals between the rows. Formulations were allowed to soak for 10 min on an orbital shaker, then 150 uL of each extraction sample was collected and transferred to a 96 well microtiter plate using a 6-channel, adjustable spacing, multichannel pipette. Each row of two sets with three replicates was collected at the same time, aspirating twice to ensure a homogenous mixture. The timing of collection for each individual formulation was held to 15 second intervals to ensure that the soaking time was precise. Fluorescence measurements (415ex/471em) of all extraction samples using a TECAN Saffire2 plate reader were taken immediately following collection.

2.2. Nano-Indentation

Depth sensing indentation, also called instrumented indentation or nanoindentation, was performed using a Hysitron TriboIndenter with automation (9 samples per run) using a diamond Berkovich tip. Since accurate determination of the elastic modulus from the indentation load-displacement responses requires flat sample surfaces, indentation was performed mostly near the center of the coated discs. Before every indent, the indenter was held in contact with the surface, to allow for piezoactuator stabilization (35 s) and drift correction (40 s), at a contact load of only 0.5 mN to prevent any deformation prior to the indentation experiment. The drift rate (typically 0.1 nm s21) was automatically determined over the last 20 s of the 40 s period. After lifting the tip up to 30 nm and re-approaching the surface (surface detection at a load of 0.5 mN), the tip was loaded to maximum load of 300 μN in 5 s, held at maximum load for 5 s and unloaded in 5 s. Nine measurements with a spacing of 60 μm apart were performed per sample and the first one was left out from the analysis to further reduce the influence of drift.

2.3. Differential Scanning Calorimetry

Thermal properties of the cured coatings were characterized using Q1000 Modulated Differential Scanning Calorimeter from TA Instruments with a cooling limit up to −90° C. About 6-8 mg of the cured film was scraped out from the disc and the following heat/cool/heat regime was used: the sample was first equilibrated at 23° C. and then cooled to −10° C. at 10° C./minute, held at −10° C. for 2 min and heated to 100° C. at 10° C./minute.

2.4. König Pendulum Hardness

König pendulum hardness was measured according to ASTM D 4366-16 by sticking two cured coated discs on a steel panel on top of which steel balls of the pendulum were placed; the result was reported in seconds.

2.5. Drying Time Measurement

Drying time was measured according to ASTM D 1640. Due to small size of the coated discs dry-to-touch time was recorded when the coating no longer adheres to the finger and does not rub up appreciably when the finger was lightly rubbed across the surface.

2.5. Measurement of Epoxy Equivalent Weight

Epoxy equivalent weight (EEW, g/eq.) of the diglycidyl ether bis-epoxymonomers and EPON 828 resin were evaluated by titrating epoxy samples with 0.0925 N solution of HBr in glacial acetic acid; 1 wt. % solution of crystal violet in acetic acid was used as an indicator. EEW value was calculated using the following equation (1) and the values are reported in Table 7, where W is the sample mass in grams, N is the normality of HBr solution, and V is the volume of HBr solution used for titration in mL.

$$EEW = \frac{100 \times W}{N \times V}$$

TABLE 7

Epoxy equivalent weight (EEW, g/eq.) of the diglycidyl ether bis-epoxymonomers and EPON 828 resin.

| Resin | | EEW (g/eq) |
|---|---|---|
| GLY 13/16 | 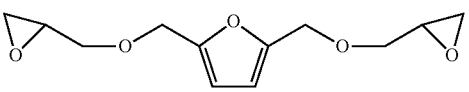 [SMILES: c1cc(COCC2CO2)oc1COCC1CO1] | 165.85 |
| GLY 23/24 | 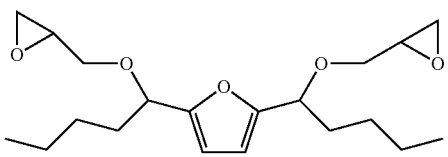 [SMILES: CCCCC(OCC1CO1)c1ccc(C(CCCC)OCC2CO2)o1] | 148.92 |

TABLE 7-continued

Epoxy equivalent weight (EEW, g/eq.) of the diglycidyl ether bis-epoxymonomers and EPON 828 resin.

| Resin | EEW (g/eq) |
|---|---|
| GLY 17 | 157.18 |
| GLY 25 | 158.23 |
| EPON 828 | 190 |

3. Results

3.1. Drying Time

Drying time was measured as a preliminary study to estimate the reactivity of the novel diglycidyl ether bis-epoxymonomers towards various amine curatives. See Table 8. Drying time of EPON 828 was measured with the curatives as a reference.

TABLE 8

Drying time of diglycidyl ether bis-epoxymonomers and EPON 828 with amine curatives.

| | Dry-to-touch time (hr.) | | | | |
|---|---|---|---|---|---|
| Amine Curatives | EPON 828 | GLY 23/24 | GLY 17 | GLY 13/16 | GLY 25 |
| TEG-DA (XTJ-504) | 16 | PS | 18 | 14 | NI |
| Jeffamine t403 | 13 | 42 | 23 | 24 | 33 |
| Jeffamine D-230 | 25 | 77 | 24 | 17 | 56 |
| Jeffamine D-400 | NI | 91 | 28 | NI | 62 |
| PACM | 8 | 18 | 22 | 15 | 19 |
| 1,3-BAC | 8 | 17 | 20 | 22 | 16 |
| IPDA | 11 | 16 | 22 | 12 | 16 |
| Xylene diamine | 5 | 22 | 28 | 13.5 | 20 |
| Diethylenetriamine | 6 | PS | 20 | 16 | 17 |
| Tetraethylenepentamine | 5 | PS | 23 | 18 | 21 |
| Priamine 1075 | PS | PS | PS | PS | PS |
| 1,8 DA Octane | 6 | 17 | 20 | 14 | 15 |

S-Phase separation
NI-Not included in the study

3.2. Dye Extraction Results

The dye extraction method described previously was used to estimate the relative crosslink density of the coatings. Higher values of dye extraction are related to lower crosslinked coatings and vice versa. The tables below show the dye extraction results for coatings made from the diglycidyl ethers and amine curing agents cured under room temperature (RT) conditions as well as at elevated temperatures for the times shown.

TABLE 9

Dye extraction results of coatings formulated from GLY 23/24 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 20578 | 20991 | 20042 | 20125 | 16544 | 15915 | 14557 |
| Jeffamine t403 | 16333 | 14895 | 14522 | 16578 | 14166 | 13552 | 15073 |
| Jeffamine D-230 | 20123 | 18786 | 19086 | 21048 | 16687 | 16101 | 17574 |
| Jeffamine D-400 | 21019 | 20998 | 21705 | 24856 | 21326 | 20358 | 21549 |
| PACM | 11116 | 10935 | 10700 | 13334 | 10545 | 9585 | 10708 |
| 1,3-BAC | 13703 | 14280 | 14332 | 16715 | 14072 | 13036 | 14344 |
| IPDA | 18306 | 13541 | 12157 | 13322 | 12930 | 11862 | 13441 |
| Xylene diamine | 15516 | 12031 | 11821 | 12910 | 13804 | 13590 | 14816 |
| Diethylenetriamine | 15139 | 14594 | 16254 | 20919 | 17731 | 19418 | 21345 |
| Tetraethylenepentamine | 17050 | 16644 | 17776 | 25250 | 22196 | 19136 | 13935 |
| Priamine 1075 | 24208 | 20580 | 20400 | 22766 | 19842 | 18530 | 19752 |
| 1,8 DA Octane | 12018 | 6414 | 5302 | 5205 | 7972 | 8954 | 7946 |

TABLE 10

Dye extraction results of coatings formulated from GLY 13/16 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 204 | 214 | 152 | 129 | 168 | 124 | 142 |
| Jeff. t403 | 3463 | 3611 | 3519 | 2492 | 2858 | 2473 | 1665 |
| Jeff. D-230 | 8819 | 9187 | 9554 | 9955 | 8043 | 7003 | 7356 |
| Jeff. D-400 | | | | NI | | | |
| PACM | 304 | 1525 | 760 | 126 | 213 | 61 | 107 |
| 1,3-BAC | 1376 | 324 | 250 | 426 | 679 | 234 | 124 |
| IPDA | 127 | 136 | 84 | 54 | 127 | 103 | 77 |
| Xylene diamine | 174 | 72 | 92 | 100 | 170 | 120 | 91 |
| DETA | 341 | 105 | 111 | 105 | 76 | 81 | 78 |
| TEPA | 703 | 126 | 748 | 148 | 548 | 166 | 525 |
| Priamine 1075 | 44637 | 45440 | 46136 | 48543 | 37621 | 33993 | 30476 |
| 1,8 DA Octane | 272 | 608 | 529 | 326 | 693 | 196 | 152 |

NI—Not included in the study

TABLE 11

Dye extraction results of coatings formulated from GLY 17 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 738 | 2114 | 2604 | 3033 | 4141 | 3087 | 2258 |
| Jeffamine t403 | 3720 | 3663 | 3703 | 2608 | 3016 | 2542 | 2072 |
| Jeffamine D-230 | 27621 | 28338 | 28333 | 27862 | 23012 | 18084 | 13276 |
| Jeffamine D-400 | 38468 | 40511 | 40735 | 40689 | 36651 | 32086 | 30629 |
| PACM | 3500 | 2994 | 2906 | 641 | 1145 | 286 | 130 |
| 1,3-BAC | 2321 | 2042 | 790 | 163 | 6012 | 5233 | 4326 |
| IPDA | 2863 | 6772 | 7299 | 702 | 1885 | 203 | 116 |
| Xylene diamine | 7401 | 1100 | 1100 | 956 | 15431 | 23468 | 13669 |
| Diethylenetriamine | 931 | 1121 | 1409 | 678 | 1363 | 309 | 342 |
| Tetraethylenepentamine | 29781 | 25886 | 25229 | 27807 | 3889 | 1879 | 1293 |
| Priamine 1075 | 44422 | 44165 | 44577 | 45501 | 40452 | 38352 | 35642 |
| 1,8 DA Octane | 20532 | 12378 | 10432 | 8193 | 6087 | 6035 | 6005 |

TABLE 12

Dye extraction results of coatings formulated from GLY 25 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | NI | | | | | | |
| Jeffamine t403 | 17277 | 16437 | 17283 | 15196 | 15751 | 15142 | 13292 |
| Jeffamine D-230 | 12654 | 13080 | 14141 | 13358 | 9596 | 10105 | 10171 |
| Jeffamine D-400 | 34037 | 35898 | 35054 | 36861 | 31008 | 28581 | 28691 |
| PACM | 3493 | 9923 | 7238 | 6320 | 11110 | 9384 | 7539 |
| 1,3-BAC | 13117 | 13626 | 13394 | 11472 | 8623 | 2590 | 1397 |
| IPDA | 15948 | 15468 | 15904 | 15007 | 13542 | 11417 | 11280 |
| Xylene diamine | 2167 | 2264 | 2782 | 1396 | 7190 | 4469 | 2173 |
| Diethylenetriamine | 9138 | 5968 | 6416 | 5996 | 1483 | 1882 | 607 |
| Tetraethylenepentamine | 14755 | 10584 | 4889 | 4971 | 867 | 879 | 820 |
| Priamine 1075 | 37500 | 32975 | 48161 | 45077 | 37220 | 35820 | 31653 |
| 1,8 DA Octane | 1124 | 1811 | 2098 | 2595 | 1704 | 726 | 679 |

NI—Not included in the study

TABLE 13

Dye extraction results of coatings formulated from EPON 828 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 8648 | 1153 | 1124 | 1358 | 1124 | 887 | 501 |
| Jeffamine t403 | 568 | 13751 | 3867 | 353 | 336 | 64 | 68 |
| Jeffamine D-230 | 1327 | 17265 | 4245 | 247 | 212 | 115 | 96 |
| PACM | 1107 | 247 | 227 | 211 | 37 | 36 | 35 |
| 1,3-BAC | 628 | 1172 | 917 | 1331 | 189 | 123 | 108 |
| IPDA | 132 | 426 | 130 | 84 | 44 | 56 | 36 |
| Xylene diamine | 8704 | 91 | 90 | 84 | 72 | 55 | 42 |
| Diethylenetriamine | 11478 | 7004 | 5431 | 3014 | 1198 | 885 | 487 |
| Tetraethylenepentamine | 18994 | 1604 | 391 | 643 | 425 | 335 | 338 |
| Priamine 1075 | 5075 | 31762 | 31543 | 29461 | 26349 | 22649 | 23601 |
| 1,8 DA Octane | 13289 | 995 | 488 | 157 | 589 | 63 | 63 |

3.3. Pendulum Hardness Results

Konig pendulum hardness measurements were carried out on the coatings made by reacting the diglycidyl ethers with the amine curing agents at room temperature (RT) and elevated temperatures for the times indicated. Higher pendulum hardness value indicates a harder coating.

TABLE 14

Pendulum hardness of coatings formulated from GLY 23/24 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | | | PS, T | | | | |
| Jeffamine t403 | 27 | 19 | 21 | 25 | 25 | 22 | 24 |
| Jeffamine D-230 | 16 | 19 | 22 | 20 | 18 | 19 | 21 |
| Jeffamine D-400 | 31 | 28 | 33 | 43 | 26 | 39 | 53 |
| PACM | 29 | 10 | 36 | 33 | 43 | 54 | 61 |
| 1,3-BAC | 8 | 5 | 11 | 14 | 7 | 11 | 15 |
| IPDA | 10 | 25 | 91 | 97 | 61 | 66 | 83 |
| Xylene diamine | 12 | 8 | 7 | 9 | 4 | 4 | 5, W |
| Diethylenetriamine | | | PS, W | | | | |
| Tetraethylenepentamine | | | | | | | |
| Priamine 1075 | | | PS, T | | | | |
| 1,8 DA Octane | 17 | 24 | 32 | 19 | 21 | 15 | 19 |

PS—Phase separated
T—Tacky
W—Wrinkled

TABLE 15

Pendulum hardness results of coatings formulated from GLY 13/16 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 8 | 7 | 7 | 7 | 11 | 17 | 19 |
| Jeffamine t403 | 75 | 59 | 134 | 143 | 44 | 154 | 153 |
| Jeffamine D-230 | 10 | 7 | 7 | 9 | 7 | 7 | 11 |
| Jeffamine D-400 | | | NI | | | | |
| PACM | 32 | 163 | 173 | 191 | 173 | 151 | 177 |
| 1,3-BAC | 7 | 13 | 20 | 23 | 61 | 95 | 108 |
| IPDA | 185 | 186 | 187 | 195 | 154 | 193 | 200 |
| Xylene diamine | 13 | 12 | 17 | 18 | 17 | 63 | 68 |
| Diethylenetriamine | 14 | 12 | 13 | 17 | 26 | 79 | 105 |
| Tetraethylenepentamine | 28 | 9 | 25 | 36 | 141 | 179 | 183 |
| Priamine 1075 | | | PS | | | | |
| 1,8 DA Octane | 15 | 16 | 18 | 13 | 17 | 22 | 28 |

NI—Not included in the study
PS—Phase separated

TABLE 16

Pendulum hardness results of coatings formulated from GLY 17 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 6 | 6 | 7 | 14 | 7 | 13 | W |
| Jeffamine t403 | 86 | 66 | 150 | 171 | 85 | 152 | 178 |
| Jeffamine D-230 | | | NI | | | | |
| Jeffamine D-400 | | | | | | | |
| PACM | 44 | 113 | 109 | 116 | 152 | 174 | 176 |
| 1,3-BAC | 39 | 38 | 36 | 42 | 71 | 140 | 173 |
| IPDA | 80 | 130 | 140 | 146 | 152 | 192 | 202 |
| Xylene diamine | 9 | 14 | 20 | 30 | 10 | 27 | 88 |
| Diethylenetriamine | 4 | 7 | 9 | 9 | 36 | 88 | 134 |
| Tetraethylenepentamine | | | NI | | | | |
| Priamine 1075 | | | PS, T | | | | |
| 1,8 DA Octane | 4 | 11 | 14 | 15 | 13 | 17 | 20 |

NI—Not included in the study
PS—Phase separated
T—Tacky

TABLE 17

Pendulum hardness results of coatings formulated from GLY 25 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | | | NI | | | | |
| Jeffamine t403 | 9 | 11 | 11 | 11 | 9 | 12 | 13 |
| Jeffamine D-230 | | | NI | | | | |
| Jeffamine D-400 | | | | | | | |
| PACM | 30 | 107 | 50 | 27 | 83 | 127 | 169 |
| 1,3-BAC | 9 | 25 | 27 | 31 | 42 | 125 | 123 |
| IPDA | 30 | 18 | 17 | 13 | 11 | 9 | 10 |
| Xylene diamine | 7 | 6 | 7 | 38 | 40 | 38 | 45 |
| Diethylenetriamine | | | NI | | | | |
| Tetraethylenepentamine | | | | | | | |
| Priamine 1075 | | | PS | | | | |
| 1,8 DA Octane | 158 | 159 | 152 | 157 | 127 | 174 | 169 |

NI—Not included in the study
PS—Phase separated

TABLE 18

Pendulum hardness of coatings formulated from EPON 828 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | 13 | 33 | 22 | 46 | 85 | 93 | 95 |
| Jeffamine t403 | 140 | 135 | 180 | 87 | 147 | 176 | 167 |
| Jeffamine D-230 | 171 | 195 | 178 | 212 | 139 | 180 | 107 |
| PACM | 151 | 107 | 160 | 159 | 155 | 157 | 153 |
| 1,3-BAC | 130 | 140 | 138 | 136 | 131 | 135 | 138 |
| IPDA | 133 | 89 | 150 | 175 | 160 | 171 | 166 |
| Xylene diamine | 56 | 49 | 104 | 92 | 118 | 137 | 134 |
| Diethylenetriamine | 9 | 35 | 44 | 48 | 78 | 107 | 117 |
| Tetraethylenepentamine | 32 | 32 | 82 | 71 | 122 | 159 | 121 |
| Priamine 1075 | | | HW | | | | |
| 1,8 DA Octane | | | | | | | |

HW—Highly Wrinkled

3.2. Results from DSC

TABLE 19

Glass transition temperature ($T_g$) of coatings formulated from GLY 23/24 with amine curatives.

| Curing Temperature (° C.) | RT | 60 | 100 |
|---|---|---|---|
| Curing Time | 7 Days | 3 h. | 3 h. |
| TEG-DA (XTJ-504) | −1 | 3 | 5 |
| Jeffamine t403 | 5 | 6 | 7 |
| Jeffamine D-230 | −1 | −1 | 12 |
| Jeffamine D-400 | −3 | 0 | 40 |
| PACM | 30 | 29 | 32 |
| 1,3-BAC | 56 | 21 | 19 |
| IPDA | 25 | 38 | 34 |
| Xylene diamine | 9 | 13 | 20 |
| Diethylenetriamine | | PS | |
| Tetraethylenepentamine | | | |
| Priamine 1075 | | | |
| 1,8 DA Octane | 13 | 12 | 15 |

PS-Phase separated

TABLE 20

Glass transition temperature ($T_g$) of coatings formulated from GLY 13/16 with amine curatives.

| Curing Temperature (° C.) | RT | 60 | 100 |
|---|---|---|---|
| Curing Time | 7 Days | 3 h. | 3 h. |
| TEG-DA (XTJ-504) | 14 | 15 | 17 |
| Jeffamine t403 | 38 | 40 | 60 |
| Jeffamine D-230 | 11 | 12 | 14 |
| Jeffamine D-400 | | NI | |
| PACM | 39 | 50 | 63 |
| 1,3-BAC | 15 | 22 | 45 |
| IPDA | 41 | 54 | 57 |
| Xylene diamine | 6 | 13 | 42 |
| Diethylenetriamine | 16 | 19 | 39 |
| Tetraethylenepentamine | 32 | 36 | 39 |
| Priamine 1075 | | PS | |
| 1,8 DA Octane | 7 | 15 | 19 |

PS-Phase separated
NI-Not included in the study

TABLE 21

Glass transition temperature (Tg) of coatings formulated from GLY 17 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | −6 | 1 | 3 | 6 | 20 | 23 | 27 |
| Jeffamine t403 | 39 | 36 | 39 | 40 | 40 | 41 | 45 |
| Jeffamine D-230 | | | NI | | | | |
| Jeffamine D-400 | | | | | | | |
| PACM | 33 | 31 | 39 | 41 | 39 | 39 | 41 |
| 1,3-BAC | 34 | 32 | 39 | 33 | 36 | 42 | 47 |
| IPDA | −8 | 41 | 42 | 42 | 42 | 52 | 59 |
| Xylene diamine | 7 | 25 | 30 | 27 | 21 | 26 | 30 |
| Diethylenetriamine | 13 | 17 | 19 | 26 | 33 | 37 | 37 |
| Tetraethylenepentamine | | | NI | | | | |
| Priamine 1075 | | | | | | | |
| 1,8 DA Octane | 29 | 8 | 16 | 26 | 26 | 27 | 30 |

NI—Not included in the study

TABLE 22

Glass transition temperature ($T_g$) of coatings formulated from GLY 25 with amine curatives.

| Curing Temperature (° C.) | RT | 60 | | | 100 | | |
|---|---|---|---|---|---|---|---|
| Curing Time | 7 Days | 1 h. | 3 h. | 6 h. | 1 h. | 3 h. | 6 h. |
| TEG-DA (XTJ-504) | | | NI | | | | |
| Jeffamine t403 | 3 | 3 | 3 | 5 | 3 | 2 | 3 |
| Jeffamine D-230 | | | NI | | | | |
| Jeffamine D-400 | | | | | | | |
| PACM | 14 | 9 | 23 | 28 | 27 | 29 | 33 |
| 1,3-BAC | 16 | 15 | 28 | 29 | 25 | 30 | 35 |
| IPDA | 33 | 17 | 20 | 29 | 31 | 33 | 35 |
| Xylene diamine | 17 | 11 | 16 | 35 | 27 | 30 | 31 |
| Diethylenetriamine | | | NI | | | | |
| Tetraethylenepentamine | | | | | | | |
| Priamine 1075 | | | | | | | |
| 1,8 DA Octane | −4 | −4 | 4 | 11 | 6 | 11 | 21 |

NI—Not included in the study

TABLE 23

Glass transition temperature ($T_g$) of coatings formulated from EPON 828 with amine curatives.

| Curing Temperature (° C.)<br>Curing Time | RT<br>7 Days | 60<br>3 h. | 100<br>3 h. |
|---|---|---|---|
| TEG-DA (XTJ-504) | 52 | 54 | 54 |
| Jeffamine t403 | 53 | 58 | 63 |
| Jeffamine D-230 | 47 | 56 | 57 |
| Jeffamine D-400 | 50 | 49 | 51 |
| PACM | 47 | 49 | 51 |
| 1,3-BAC | 44 | 46 | 48 |
| IPDA | 48 | 53 | 55 |
| Xylene diamine | 53 | 60 | 61 |
| Diethylenetriamine | 53 | 58 | 62 |
| Tetraethylenepentamine | 23 | 34 | 39 |
| Priamine 1075 | 36 | 45 | 54 |
| 1,8 DA Octane | 52 | 55 | 61 |

3.2. Results from Nano-Indentation

TABLE 24

Hardness (GPa) of coatings formulated from GLY 23/24, GLY 13/16, GLY 17 and EPON 828 with amine curatives.

| Resin | Curing Temperature (° C.)<br>Curing Time | RT<br>7 Days | 60<br>1 hr. | 60<br>3 hr. | 60<br>6 hr. | 100<br>1 hr. | 100<br>3 hr. | 100<br>6 hr. |
|---|---|---|---|---|---|---|---|---|
| GLY 23/24 | TEG-DA (XTJ-504) | | | | PS | | | |
| | Jeffamine t403 | 1.94 | 1.85 | 2.07 | 1.57 | 1.78 | 1.80 | 1.39 |
| | Jeffamine D-230 | | | | S | | | |
| | Jeffamine D-400 | | | | | | | |
| | PACM | 51.25 | 2.59 | 8.26 | 16.46 | 35.72 | 25.55 | 108.96 |
| | 1,3-BAC | 1.37 | 1.25 | 6.72 | 7.25 | 1.34 | 2.54 | 2.55 |
| | IPDA | 67.34 | 5.38 | 140.12 | 152.38 | 46.27 | 21.76 | 94.22 |
| | Xylene diamine | — | 39.09 | — | — | — | — | — |
| | Diethylenetriamine | | | | PS | | | |
| | Tetraethylenepentamine | | | | | | | |
| | Priamine 1075 | | | | | | | |
| | 1,8 DA Octane | 49.40 | 12.29 | 51.43 | 4.42 | 2.18 | 1.95 | 1.79 |
| GLY 17 | Jeffamine t403 | 222.06 | 3.71 | 46.69 | 260.36 | 167.28 | 146.40 | 268.56 |
| GLY 13/16 | Jeffamine t403 | 223.28 | 38.88 | 131.89 | 274.07 | 158.80 | 154.26 | 286.52 |
| | PACM | 225.24 | 299.19 | 221.63 | 362.53 | 244.32 | 253.11 | 332.73 |
| | 1,3-BAC | 24.39 | 13.43 | 391.02 | 207.58 | 273.34 | 481.07 | 528.59 |
| EPON 828 | TEG-DA (XTJ-504) | — | 130.70 | 102.86 | — | — | — | — |
| | Jeffamine t403 | 323.52 | 204.75 | 255.74 | 258.47 | 263.74 | 500.88 | 461.72 |
| | Jeffamine D-230 | 250.55 | 329.57 | 258.18 | 321.79 | 338.59 | 242.51 | 333.55 |
| | PACM | 440.05 | 263.58 | 286.69 | 303.08 | 372.51 | 361.02 | 650.28 |
| | 1,3-BAC | 76.12 | 256.54 | 261.43 | 303.91 | 131.72 | 106.13 | 162.60 |
| | IPDA | 163.59 | 237.80 | 290.40 | 468.67 | 507.07 | 298.58 | 459.19 |
| | Xylene diamine | 176.39 | 91.36 | 98.11 | 149.09 | 214.12 | 228.24 | 141.20 |
| | Diethylenetriamine | 7.55 | 145.96 | 156.02 | 48.15 | 395.40 | 178.75 | 419.54 |
| | Tetraethylenepentamine | 129.76 | 104.91 | 331.80 | 103.05 | 428.99 | 324.58 | 472.33 |
| | Priamine 1075 | | | | PS | | | |
| | 1,8 DA Octane | | | | HW | | | |

PS—Phase separated
S—Soft, sticky surface
HW—Highly wrinkled

TABLE 25

Reduced elastic modulus (9MPa) of coatings formulated from GLY 23/24, GLY 13/16, GLY 17 and EPON 828 with amine curatives.

| Resin | Curing Temperature (° C.)<br>Curing Time | RT<br>7 Days | 60<br>1 hr. | 60<br>3 hr. | 60<br>7 Days | 100<br>1 hr. | 100<br>3 hr. | 100<br>7 Days |
|---|---|---|---|---|---|---|---|---|
| GLY 23/24 | TEG-DA (XTJ-504) | | | | PS | | | |
| | Jeffamine t403 | 11.2 | 5.6 | 9.5 | 9.3 | 7.8 | 8.1 | 8.3 |
| | Jeffamine D-230 | | | | S | | | |
| | Jeffamine D-400 | | | | | | | |
| | PACM | 5.3 | 5.5 | 3.4 | 5.4 | 3.0 | 2.2 | 5.3 |
| | 1,3-BAC | 50.4 | 45.1 | 65.8 | 125.1 | 38.1 | 45.4 | 118.0 |

TABLE 25-continued

Reduced elastic modulus (9MPa) of coatings formulated from GLY 23/24, GLY 13/16, GLY 17 and EPON 828 with amine curatives.

| Resin | Curing Temperature (° C.) Curing Time | RT 7 Days | 60 1 hr. | 60 3 hr. | 60 7 Days | 100 1 hr. | 100 3 hr. | 100 7 Days |
|---|---|---|---|---|---|---|---|---|
| | IPDA | 2.7 | 303.0 | 3.3 | 2.3 | 4.0 | 5.1 | 3.2 |
| | Xylene diamine | — | 420.3 | — | — | — | — | — |
| | Diethylenetriamine | | | | PS | | | |
| | Tetraethylenepentamine | | | | | | | |
| | Priamine 1075 | | | | | | | |
| | 1,8 DA Octane | 587.7 | 122.5 | 2.7 | 52.4 | 11.2 | 9.5 | 9.2 |
| GLY 17 | Jeffamine t403 | 4.6 | 1.2 | 4.4 | 4.3 | 4.7 | 4.3 | 5.4 |
| GLY 13/16 | Jeffamine t403 | 5.0 | 7.1 | 4.6 | 5.6 | 3.4 | 4.4 | 5.6 |
| | PACM | 5.3 | 5.5 | 3.4 | 5.4 | 3.0 | 2.2 | 5.3 |
| | 1,3-BAC | 362.6 | 310.1 | 5.2 | 8.2 | 5.0 | 8.8 | 7.9 |
| EPON 828 | TEG-DA (XTJ-504) | — | 189.1 | 252.8 | — | — | — | — |
| | Jeffamine t403 | 7.1 | 4.4 | 5.1 | 4.7 | 4.9 | 7.3 | 8.3 |
| | Jeffamine D-230 | 5.9 | 6.3 | 5.0 | 6.2 | 6.3 | 4.5 | 6.5 |
| | PACM | 9.8 | 4.5 | 4.8 | 4.4 | 4.9 | 5.1 | 10.0 |
| | 1,3-BAC | 1.9 | 5.0 | 4.4 | 3.0 | 3.7 | 2.9 | 3.9 |
| | IPDA | 4.5 | 4.5 | 4.8 | 6.1 | 6.8 | 4.6 | 6.1 |
| | Xylene diamine | 3.9 | 3.3 | 3.1 | 12.6 | 4.4 | 5.4 | 4.1 |
| | Diethylenetriamine | 309.7 | 2.8 | 1.8 | 1.3 | 5.5 | 48.6 | 8.2 |
| | Tetraethylenepentamine | 3.3 | 2.4 | 5.1 | 2.0 | 6.4 | 4.4 | 8.4 |
| | Priamine 1075 | | | | PS | | | |
| | 1,8 DA Octane | | | | HW | | | |

PS—Phase separated
S—Soft, sticky surface
HW—Highly wrinkled

The invention claimed is:

1. A diglycidyl ether having the following structure:

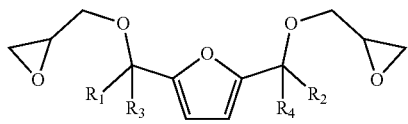

wherein $R_1$, $R_2$, $R_3$, and $R_4$ are independently selected from the group consisting of H, $C_1$-$C_6$ alkyl, $C_1$-$C_6$ alkenyl, aryl, and $C_1$-$C_6$alkyl-aryl, with the proviso that $R_1$, $R_2$, $R_3$, and $R_4$ cannot all be H.

2. The diglycidyl ether of claim 1 having the following structure:

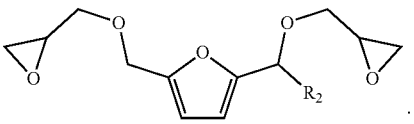

3. The diglycidyl ether of claim 2, wherein $R_2$ is methyl or phenyl.

4. The diglycidyl ether of claim 1 having the following structure:

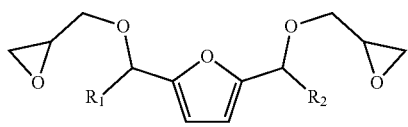

5. The diglycidyl ether of claim 4, wherein $R_1$ and $R_2$ are both methyl, n-butyl, or allyl.

6. The diglycidyl ether of claim 1 having the following structure:

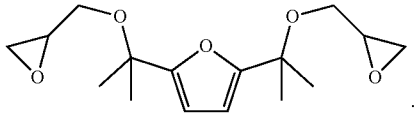 [SMILES: CC(C)(OCC1CO1)c1ccc(C(C)(C)OCC2CO2)o1]

7. A method for making the diglycidyl ether of claim 1, comprising, consisting essentially of, or consisting of:
reacting a diol with epichlorohydrin under conditions sufficient to form the diglycidyl ether,
wherein the diol has the following structure:

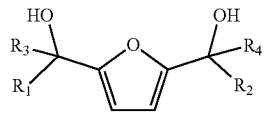

wherein $R_1$, $R_2$, $R_3$, and $R_4$ are independently selected from the group consisting of H, $C_1$-$C_6$alkyl, $C_1$-$C_6$ alkenyl, aryl, and $C_1$-$C_6$alkyl-aryl.

8. A curable coating composition comprising, consisting essentially of, or consisting of:
a) at least one diglycidyl ether of claim 1; and
b) an amine.

9. The curable coating composition of claim 8, wherein the amine is an aliphatic, an aromatic, a cycloaliphatic, or a polyether amine.

10. The curable coating composition of claim 9, wherein the aliphatic amine is dimer diamine, 1,8-diaminooctane, diethylenetriamine, or tetraethylenepentamine.

11. The curable coating composition of claim 9, wherein the aromatic amine is m-xylylenediamine.

12. The curable coating composition of claim 9, wherein the cycloaliphatic amine is 1,3-bis(aminomethyl)cyclohexane, isophorone diamine, or bis(p-aminocyclohexyl)methane.

13. A composite or adhesive comprising, consisting essentially of, or consisting of at least one diglycidyl ether of claim 1.

* * * * *